US012799511B2

(12) United States Patent
Chaubey et al.

(10) Patent No.: US 12,799,511 B2
(45) Date of Patent: Nov. 17, 2026

(54) **PROCESS FOR THE PREPARATION OF TETRAHYDROANTHRACENES FROM *STREPTOMYCES* SPP. AND ANTICANCER ACTIVITY THEREOF**

(71) Applicant: Council of Scientific and Industrial Research, New Delhi (IN)

(72) Inventors: Asha Chaubey, Jammu (IN); Ravi Singh Manhas, Jammu (IN); Jasmine Kour Khosla, Jammu (IN); Ajaz Ahmed, Jammu (IN); Syed Mudabir Ahmad, Jammu (IN); Harshita Tiwari, Jammu (IN); Amit Nargotra, Jammu (IN); Debaraj Mukherjee, Jammu (IN); Anindya Goswami, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 192 days.

(21) Appl. No.: 18/703,696

(22) PCT Filed: Sep. 12, 2022

(86) PCT No.: PCT/IN2022/050812
§ 371 (c)(1),
(2) Date: Apr. 22, 2024

(87) PCT Pub. No.: WO2023/067617
PCT Pub. Date: Apr. 27, 2023

(65) Prior Publication Data

US 2025/0230477 A1 Jul. 17, 2025

(30) Foreign Application Priority Data

Oct. 20, 2021 (IN) ............................. 202111047805

(51) Int. Cl.
*C12P 15/00* (2006.01)
*A61K 31/122* (2006.01)
*A61P 35/04* (2006.01)
*C12N 1/205* (2026.01)
*C12R 1/465* (2006.01)

(52) U.S. Cl.
CPC ............ *C12P 15/00* (2013.01); *A61K 31/122* (2013.01); *A61P 35/04* (2018.01); *C12N 1/205* (2021.05); *C12R 2001/465* (2021.05)

(58) Field of Classification Search
CPC ............... C12N 1/20; C12P 1/06; C12P 15/00
See application file for complete search history.

(56) References Cited

U.S. PATENT DOCUMENTS

| | | | |
|---|---|---|---|
| 4,283,390 A | 8/1981 | Koch et al. | |
| 4,410,628 A | 10/1983 | Koch et al. | |
| 4,452,741 A | 6/1984 | Koch et al. | |
| 2025/0230477 A1* | 7/2025 | Chaubey | C12P 15/00 |

FOREIGN PATENT DOCUMENTS

CN 108821959 A 11/2018

OTHER PUBLICATIONS

S. Omura et al., "A New Antibiotic Setomimycin, Produced by a Strain of Streptomyces." The Journal of Antibiotics, vol. 31, No. 11, pp. 1091-1098, 1978. https://doi.org/10.7164/antibiotics.1091.

K. Kakinuma et al., "Structure and Biosynthesis of Setomimycin, A Novel 9, 9'-Bianthryl Antibiotic." Journal of the American Chemical Society, vol. 102 (25), pp. 7493-7498, 1980. https://doi.org./10.1021/ja00545a016.

L. T-H. Tan et al., "Investigation of Antioxidative and Anticancer Potentials of *Streptomyces* Sp. Mum256 Isolated from Malaysia Mangrove Soil." Frontiers in Microbiology, vol. 6, pp. 1316, 2015, 2 pages. https://doi.org/10.3389/fmicb.2015.01316.

J. Wang et al., "Dimeric Tetrahydroanthracene Regioisomers and Their Monomeric Precursor Produced by Streptomyces Fumigatiscleroticus HDN10255." Journal of Natural Products, vol. 83(9), pp. 2797-2802, 2020. https://doi.org/10.1021/acs.jnatprod.0c00805.

J-S. Park et al., "Genome Analysis of Streptomyces Nojiriensis JCM 3382 and Distribution of Gene Clusters for Three Antibiotics and an Azasugar Across the Genus *Streptomyces*." Microorganisms, vol. 9(9), pp. 1802, 2021, 42 pages. https://doi.org/10.3390/microorganisms9091802.

I. Kaweewan et al., "Isolation and Structure Determination of a New Cytotoxic Peptide, Curacozole, from Streptomyces Curacoi Based on Genome Mining." The Journal of Antibiotics, vol. 72(1), pp. 1-7, 2018. https://doi.org/10.1038/s41429-018-0105-4.

(Continued)

*Primary Examiner* — Tekchand Saidha
(74) *Attorney, Agent, or Firm* — BLANK ROME LLP

(57) ABSTRACT

*Streptomyces* sp. MTCC-25420 and *Streptomyces* sp. MTCC-25512 isolated from the Shivalik region of India, has been demonstrated for tetrahydroanthracene antibiotics including setomimycin production. Combination of specific physico-chemical conditions have led to the antibiotic complex formation (upto 5.0 g/L) in 2-10 days of fermentation with maximum production at 4-8 days in shake flask as well as 5 L to 500 L stirred tank bioreactors using modified production media in combination with additional carbon/nitrogen/minerals and elicitations with yields upto 800 mg/L of are 9,9' bianthracene antibiotic setomimycin. Setomimycin significantly abrogated cancer cell proliferation and inhibited cancer cell migration and invasion in highly metastatic cancer cells (MiaPaca-2, MCF-7, HT-29 and HCT-116) of Pancreatic, Breast and Colorectal origin by down regulating ERK and MEK proteins which are the major regulators of cell proliferation, differentiation and apoptosis. Interestingly setomimycin upregulated pro-apoptotic protein Par-4 and downregulated anti-apoptotic protein BCL-2 in Colon as well as breast cancer cells HCT-116 and MCF-7 respectively. Strong affinity of setomimycin towards MEK protein has been confirmed by molecular docking studies and Western blot analysis.

14 Claims, 3 Drawing Sheets

Specification includes a Sequence Listing.

(56) References Cited

OTHER PUBLICATIONS

A. Präg et al., "Regio- and Stereoselective Intermolecular Oxidative Phenol Coupling in Streptomyces." Journal of the American Chemical Society, vol. 136, pp. 6195-6198, 2014. https://doi.org/10.1021/ja501630w.
O. G. Mohamed et al., "Lincolnenins A-D: Isomeric Bactericidal Bianthracenes form Streptomyces Lincolnensis." The Journal of Organic Chemistry, pp. A-H, 2020. https://doi.org/10.1021/acs.joc.0c02492.
A.L. Staley et al., "Spectomycins, New Antibacterial Compounds Produced by Streptomyces Spectabilis: Isolation, Structures, and Biosynthesis." The Journal of Antibiotics, vol. 47, No. 12, pp. 1425-1433, 1994. https//doi.org/10.7164/antibiotics.47.1425.
International Search Report and Written Opinion for PCT/IN2022/050812 mailed Jan. 9, 2023. 9 pages.

* cited by examiner

1
Compound 1

2
Compound 2

3
Compound 3

SEQUENCE LISTING

```
Sequence total quantity: 2
SEQ ID NO: 1          moltype = DNA  length = 20
FEATURE               Location/Qualifiers
source                1..20
                      mol_type = other DNA
                      organism = synthetic construct
SEQUENCE: 1
agagtttgat cctggctcag                                    20

SEQ ID NO: 2          moltype = DNA  length = 19
FEATURE               Location/Qualifiers
source                1..19
                      mol_type = other DNA
                      organism = synthetic construct
SEQUENCE: 2
ggctaccttg ttacgactt                                     19
```

PROCESS FOR THE PREPARATION OF TETRAHYDROANTHRACENES FROM *STREPTOMYCES* SPP. AND ANTICANCER ACTIVITY THEREOF

RELATED APPLICATIONS

This application is a national phase of PCT/IN2022/050812, filed on Sep. 12, 2022, which claims priority to IN Application No. 202111047805, filed on Oct. 20, 2021. The contents of these applications are hereby incorporated by reference in their entirety.

REFERENCE TO A SEQUENCE LISTING SUBMITTED AS AN XML FILED VIA PATENT CENTER

The official copy of the sequence listing is submitted electronically via Patent Center as an XML formatted sequence listing with a file named 18703696_SEQUENCE LISTING FILE.xml, created on Oct. 8, 2024 and having a size of 3 kilabytes, and is filed concurrently with the specification. The sequence listing contained in this XML formatted document is part of the specification and is herein incorporated by reference in its entirety

FIELD OF THE INVENTION

Present invention relates to a process for the preparation of tetrahydroanthracenes of formula 1 from *Streptomyces* species [MTCC-25420 and MTCC-25512]. Present invention further relates to tetrahydroanthracenes of formula I for anticancer activity.

Formula I

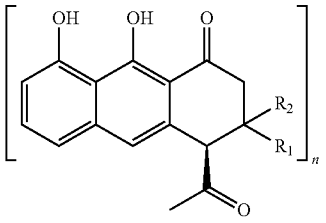

wherein n=1 or 2 and $R_1$=$CH_3$; $R_2$=OH

Particularly, present invention relates to 9,9'-bianthrylanthracene antibiotic, Setomimycin of formula 1, having activity against Gram positive bacteria has also been demonstrated to have significant anticancer activity against several cancer cell lines.

BACKGROUND OF THE INVENTION

Biaryl preanthraquinones, represented by the julichromes, spectomycins, and setomimycins, are antibiotics isolated from bacteria (doi.org/10.1021/acs.jnatprod.0c00805). In nature, intermolecular oxidative phenol coupling is the main process for the formation of a troposelective biaryl compounds. The monomeric subunits of these biarylic preanthraquinones are derived from a common polyketide precursor, yet the coupling reaction proceeds in a regioselective manner, with the position of attachment of the two subunits depending on the specific streptomycete strain (doi.org/10.1021/ja501630w).

Anthracene derivatives have hydroxyl groups such as 1-hydroxyanthracene and 2-hydroxyanthracene, homologous to phenol or naphthols and hydroxyanthracene are pharmacologically active. Many Anthracenes can also be found with multiple hydroxyl groups such as 9, 10-dihydroxyanthracene.

Setomimycin, a rare 9,9'-bianthrylanthracene antibiotic, was first isolated from *Streptomyces pseudovenezuelae* in 1978 (doi.org/10.7164/antibiotics.31.1091). It was reported to be active against Gram positive bacteria i.e. *S. aureus, B. subtilis, B. cereus*, and *M. smegmatis*, including mycobacteria. It was also shown to reduce tumor growth in a Sarcoma-180 mouse solid tumor model when administered at a dose of 200 mg/kg per day for seven days.

One of the studies showed that under certain conditions *Streptomyces lincolnensis* ACM-4234 produce a new series of bianthracenes, leading to the isolation and structure elucidation of the Lincolnenins A-D natural products. Staley in 1994 discovered three new tetrahydroanthracene antibiotics that are isolated from culture broths of *Streptomyces spectabilis* (doi.org/10.1021/acs.joc.0c02492).

Spectomycins A1, A2 and B1, have been reported as symmetrical dimeric forms $C_{38}H_{34}O_{14}$ (B1) and monomeric $C_{20}H_{20}O_7$ (A1), $C_{19}H_{18}O_7$ (A2). (doi.org/10.7164/antibiotics.47.1425).

Another report revealed Spectomycin B1, a closely related dimeric dihydroanthracene antibiotic from *Streptomyces spectabilis* UC 2294 (doi.org/10.1021/ja501630w).

Yet another study disclosed four new derivatives of tetrahydroanthracene and antibiotic (A-39183A), from the *Streptomyces fumigatiscleroticus* HDN10255. (doi.org/10.1021/acs.jnatprod.0c00805 and doi.org/10.7164/antibiotics.47.1425)

Another study revealed Antibiotic A-39183 complex, comprising microbiologically active, related factors A, B, C, D, and E, produced by submerged, aerobic fermentation of a new microorganism *Streptomyces* sp., NRRL 12049. The A-39183 factors were demonstrated to have antibacterial activity, against *Staphylococcus* and *Streptococcus* species that are penicillin resistant. The A-39183 factor ionophores were found active against both Gram-positive and Gram-negative anaerobic bacteria (U.S. Pat. Nos. 4,283,390, 4,452,741, 4,410,628).

Till date, only four strains namely *Streptomyces pseudovenezuelae* (doi.org/10.7164/antibiotics.31.1091), *Streptomyces* sp., NRRL 12049 (U.S. Pat. No. 4,283,390), *Streptomyces afghaniensis, Streptomyces auranticus* JA 4570 (doi.org/10.1021/ja501630w) have been reported for tetrahydroanthracenes and Setomimycin (9,9'-bianthracene antibiotic) production. The available prior art demonstrates the production of tetrahydroanthracenes by submerged aerobic fermentation with the yields upto 150 mg/L setomimycin production, thus, limiting its commercial exploitation. Further, none of the reports have demonstrated anticancer activity of the same.

OBJECTS OF THE INVENTION

Main objective of the present invention is to provide an improved and efficient process for the preparation of tetrahydroanthracenes of Formula I from new source i.e. *Streptomyces* sp. MTCC-25420 and *Streptomyces* sp. MTCC-25512 isolated from lower Shivalik region of North-Western Himalayas, Jammu, India.

Another objective of the present invention is to provide an improved and efficient process for the preparation of tetrahydroanthracenes of Formula I in terms of time of production as well as yields.

Still another objective of the present invention is to demonstrate the effect of Compounds 1-3 on a panel of anticancer cell lines.

Yet another objective of the present invention is to provide the mode of action of Setomimycin (Compound 3) on anticancer target proteins that regulate cell proliferation, differentiation and apoptosis.

Details of the Biological Material Used

Tetrahydroanthracene producing strains *Streptomyces* sp. MTCC-25420 and *Streptomyces* sp. MTCC-25512 used herein, were isolated from soil sample collected from Shivalik region of North-Western Himalayas, Jammu 32.7266° N, 74.8570° E, India. The *Streptomyces* sp. MTCC-25420 strain was deposited pursuant to the Budapest Treaty with the microbial culture collection repository of the CSIR-Institute of Microbial Technology (Chandigarh, India) on Dec. 7, 2020. The *Streptomyces* sp. MTCC-25512 strain was deposited pursuant to the Budapest Treaty with the microbial culture collection repository of the CSIR-Institute of Microbial Technology (Chandigarh, India) on Mar. 7, 2022.

All other biological raw materials used as media components in the invention was procured from HIMEDIA, Laboratories Pvt. Ltd 23, Vadhani Ind. Est., LBS Marg, Mumbai-400086, India.

SUMMARY OF THE INVENTION

Figure 1:
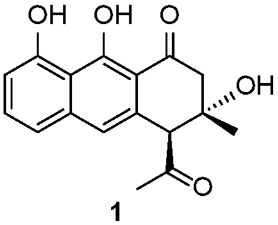
FIG. 1 represents the chemical structures of Tetrahydroanthracenes (Structure 1-3) from *Streptomyces* sp. MTCC-25420 and *Streptomyces* sp. MTCC-25512.
Figure 1:
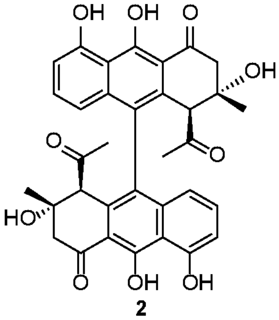
Figure 1:
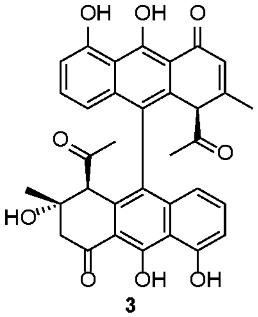

Accordingly, present invention provides a process for the preparation of tetrahydroanthracene compounds of Formula I Formula I

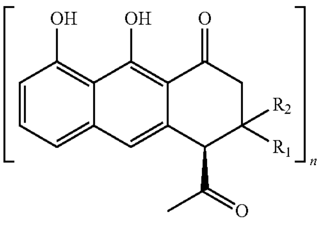

wherein n=1 or 2 and $R_1$=$CH_3$; $R_2$=OH from *Streptomyces* sp. MTCC-25420 and *Streptomyces* sp. MTCC-25512 comprising the steps of:

i. isolating the culture of *Streptomyces* sp. MTCC-25420 and *Streptomyces* sp. MTCC-25512 from soil sample collected from Shivalik foothills 32.7266° N, 74.8570° E, Jammu, India;

ii. transferring 5-10% of two days old seed culture of *Streptomyces* sp. MTCC-25420 and *Streptomyces* sp. MTCC-25512 as obtained in step (i) to production medium containing 1 to 10% w/v carbon source, nitrogen source and trace salts at pH in the range of 4.0 to 10.0 followed by incubating at a temperature in the range of 15 °C-45 °C for a period in the range of 2-10 days on a rotating shaker at speed in the range of 50-400 rpm to obtain fermented broth;

iii. liquid-liquid extract of fermented broth as obtained in step (ii) using selected solvents from the group comprising methanol-ethyl acetate, ethylacetate-toluene or acetone-toluene to obtain tetrahydroanthracenes 200 mg-5 g/L of Formula I;

iv. purifying the extract obtained from step (iii) by gravity column chromatography/preparatory HPLC to get tetrahydroanthracenes of formula I (Compound 1:2-80 mg/L; Compound 2:6-280 mg/L; Compound 3:20-800 mg/L).

In an embodiment of the present invention, tetrahydroanthracenes of formula I is selected from the group comprising:

Compound 1

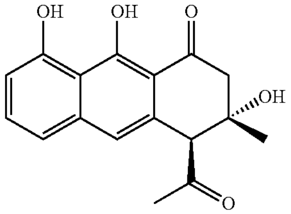

4-acetyl-3,8,9-trihydroxy-3-methyl-3,4-dihydroanthracen-1(2H)-one

Compound 2

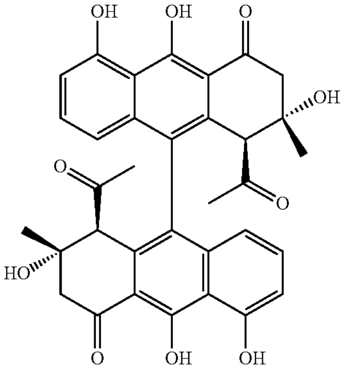

1,1′-diacetyl-2,2′,5,5′,10,10′-hexahydroxy-2,2′-dimethyl-2,2′,3,3′-tetrahydro-[9,9′-bianthracene]-4,4′(1H,1′H)-dione -continued Compound 3

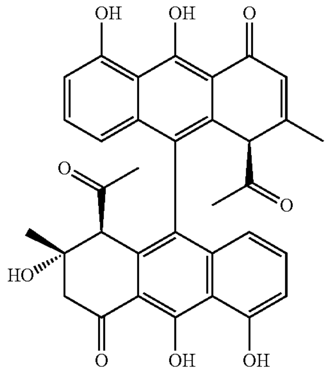

1,1′-diacetyl-2,5,5′,10,10′-pentahydroxy-2,2′-dimethyl-2,3-dihydro-[9,9′-bianthracene]-4,4′(1H,1′H)-dione In yet another embodiment of the present invention, carbon source is selected from the group comprising monosaccharides, disaccharides and polysaccharides like Glucose, Fructose, Sucrose, Mannitol, Glycerol, gluconic acid, Pectin, Lactose, Maltose, Mannose, Chitosan, Dextrin, molasses, Starch, Xylose, Molasses, Corn steep liquor, Inositol, Chitin, Sorbitol either alone or combination thereof.

In yet another embodiment of the present invention, nitrogen sources is selected from the group comprising Beef extract, Meat solubles, corn meal, Casein, Soyabean Meal, Yeast extract, N/Z amine A, N/Z amine B, Casein hydrolysate, enzyme-hydrolyzed casein, Peptone, Sodium nitrate, Valine, Ammonium nitrate, Urea, Arginine, Asparagine, Ammonium phosphate, Potassium nitrate, Ammonium sulphate, nitrate salts either alone or combination thereof.

In yet another embodiment of the present invention, trace salts are selected from the group comprising Calcium carbonate, Magnesium sulphate, Di-potassium hydrogen phosphate, Ferrous sulphate, Potassium chloride and Sodium chloride, Ammonium sulphate/nitrate.

In yet another embodiment of the present invention, Compounds 1-3 have potent anticancer activity in various cancer cell lines such as breast cancer (MCF-7, MDA-MB231), Human lung cancer (A-549), human pancreatic cancer (MiaPaca-2), Human prostate cancer (PC-3), Colon cancer cell line (HCT-116, HT 29).

In yet another embodiment of the present invention, Setomimycin i.e. Compound 3 significantly abrogated cancer cell proliferation and inhibited cancer cell migration and invasion in highly metastatic cancer cells (MiaPaca-2, MCF-7, HT-29 and HCT-116) of Pancreatic, Breast and Colorectal origin.

In yet another embodiment of the present invention, Setomimycin i.e. Compound 3 down-regulates ERK and MEK proteins which are the major regulators of cell proliferation, differentiation and apoptosis, alongside it upregulates pro-apoptotic protein Par-4 and downregulated anti-apoptotic protein BCL-2 in Colon as well as breast cancer cells HCT-116 and MCF-7 respectively, and molecular docking studies and western blot analysis further support strong affinity of setomimycin towards MEK protein.

In yet another embodiment of the present invention, Compounds 1-3 have potent antimicrobial activity against a panel of Gram positive human pathogens such as *Staphylococcus aureus, Bacillus subtilis, Bacillus cereus, Micrococcus luteus* and MRSA/MDRs.

DETAILED DESCRIPTION OF THE INVENTION

Present invention provides a process for the preparation of tetrahydroanthracenes of Formula I from *Streptomyces* sp. MTCC-25420 and *Streptomyces* sp. MTCC-25512 and anticancer activity thereof, which comprises specific fermentation conditions in combination for production of tetrahydroanthracenes of Formula I upto 5.0 g/L and upto 800 mg/L yields of setomimycin of formula 3 or even higher in presence of certain elicitors/precursors, wherein, Setomimycin (Compound-3) significantly abrogated cancer cell proliferation and inhibited cancer cell migration and invasion in highly metastatic cancer cells (MiaPaca-2, MCF-7, HT-29 and HCT-116) of Pancreatic, Breast and Colorectal origin.

Formula I

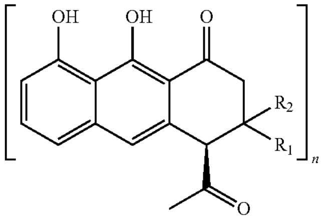

wherein n=1 or 2 and $R_1$=$CH_3$; $R_2$=OH

Present invention provides a process for the preparation of Tetrahydroanthracenes of Formula I, including rare 9,9'-bianthrylanthracene antibiotic Setomimycin (Compound-3) from new source i.e. *Streptomyces* sp. MTCC-25420 and *Streptomyces* sp. MTCC-25512 from NW Himalayan region.

The process for the production of tetrahydroanthracenes of Formula I involves solid state as well as submerged fermentation, wherein consistent extracellular as well as intracellular production takes place in various fermentation media in shake flask as well as in bioreactor upto 500 L size, under various fermentation conditions (either alone or in combination).

Essential trace elements salts like Calcium carbonate, Magnesium sulphate, Di-potassium hydrogen phosphate, Ferrous sulphate, Potassium chloride and Sodium chloride, Ammonium sulphate/nitrate etc. are necessary in combination with various constituents of fermentation media for the growth of the organism and production of tetrahydroanthracenes.

The tetrahydroanthracene producers, i.e. *Streptomyces* sp. MTCC-25420 and *Streptomyces* sp. MTCC-25512 are capable to grow at pH 4.0 to pH 10.0 with Setomimycin production at wide pH range i.e. pH 5.0, 6.0, 7.0, 8.0, and 9.0 with preferred pH of 6.0 to 8.0.

*Streptomyces* sp. MTCC-25420 and *Streptomyces* sp. MTCC-25512 grow at temperatures ranging from 15 °C to 45 °C with the preferred temperature for Formula-1 production at 20 °C to 40 °C.

*Streptomyces* sp. MTCC-25420 and *Streptomyces* sp. MTCC-25512 provide the production of tetrahydroanthracenes (Formula-1) within 2-10 days depending on the production medium and fermentation conditions with the yield of crude extract ranging from 200 mg/L to 5.0 g/L or even higher in presence of certain elicitors/precursors e.g. Valine, Arginine, Asparagine, Sodium acetate and Glycerol.

Antibiotic (Compounds 1-3) has potent antimicrobial activity against a panel of Gram positive human pathogens such as *Staphylococcus aureus, Bacillus subtilis, Bacillus cereus, Micrococcus luteus* and Methicillin-resistant *Staphylococcus aureus* (MRSA)/Multi drug resistant bacteria (MDRs).

Compounds 1-3 have shown potent anticancer activity against various cancer cell lines such as breast cancer (MCF-7, MDA-MB231), Human lung cancer (A-549), human pancreatic cancer (MiaPaca-2), Human prostate cancer (PC-3), Colon cancer cell line (HCT-116, HT-29). Wherein, Setomimycin (Compound-3) significantly abrogated cancer cell proliferation and inhibited cancer cell migration and invasion in highly metastatic cancer cells (MiaPaca-2, MCF-7, HT-29 and HCT-116) of Pancreatic, Breast and Colorectal origin.

The culture was maintained on glass test tube of 18×150 $mm^2$ size having agar slants (Table 1) by transferring a loopful of culture from matured slant and kept for incubation at 28 °C±2 °C for about one week with subsequent sub-culturing after every two weeks. The Pre-inoculum was prepared in a narrow mouth 500 mL Erlenmeyer flask containing 150 mL medium (Table 2) by transferring loopful of freshly grown culture.

The inoculated medium was incubated at about 28 °C±2 °C for about 48-72 hours on a rotating shaker at 250 rpm. 5-10% of pre inoculum was transferred to 1000 mL Erlenmeyer flasks containing 300 mL seed medium (Table 3). The inoculum was prepared by incubating the flasks at 28 °C±2 °C for about 48-72 hours on a rotating shaker at 250 rpm.

Preferably 5-10% of two days old seed culture (inoculum) was transferred to 1000 mL Erlenmeyer flasks containing 300 mL production media (Table 4) and incubated at 15 °C-45 °C for 2-10 days on a rotating shaker at 100-300 rpm followed by liquid-liquid extraction using methanol-ethyl acetate or ethyl acetate-hexane or ethyl acetate-toluene, acetone-toluene or methanol-dichloromethane or methanol-chloroform or ethyl acetate-acetone or combination of these.

Monosaccharides, disaccharides and polysaccharides including Glucose, Fructose, Sucrose, Mannitol, Glycerol, Pectin, Lactose, Maltose, Mannose, Gluconic acid, Chitosan, Dextrin, Starch, Xylose, Molasses, Corn steep liquor, Inositol, Chitin, Sorbitol etc. are useful for the production of tetrahydroanthracenes; wherein, preferred carbon sources are glucose, starch, dextrin, chitosan, molasses, gluconic acid and glycerol either alone or combinations of these nutrients. Among these, glycerol and starch is most preferable carbon sources for antibiotic production or in combinations with, soyabean meal, sodium acetate, glycerol and glucose.

Organic as well as inorganic nitrogen sources like Beef extract, Casein, Soya Meal, Oatmeal, Yeast extract, N/Z amine A, N/Z amine B, Casein hydrolysate, Peptone, Sodium nitrate, Valine, Ammonium nitrate, Urea, Arginine, Asparagine, Ammonium phosphate, Potassium nitrate, Ammonium sulphate support tetrahydroanthracenes production; wherein preferred nitrogen sources are soybean meal, yeast extract, peptone, sodium/potassium nitrate, casein, casein hydrolysate and ammonium nitrate or combinations of these nutrients. Meat solubles, peptone, Beef extract, corn meal, enzyme-hydrolyzed casein, and nitrate salts are also useful.

Trace elements salts like Calcium carbonate, Magnesium sulphate, Di-potassium hydrogen phosphate, Ferrous sulphate, Potassium chloride and Sodium chloride, Ammonium sulphate/nitrate etc. are helpful in combination for the growth of the organism and production of tetrahydroanthracenes.

Setomimycin (Compound-3) has potent antimicrobial activity against a panel of Gram positive human pathogens such as *Staphylococcus aureus, Bacillus, subtilis, Bacillus cereus, Micrococcus luteus* and Methicillin-resistant *Staphylococcus aureus* (MRSA)/Multi drug resistant bacteria (MDRs).

The antibiotic Setomimycin (Compound-3) has potent anticancer activity against various cancer cell lines viz. breast cancer (MCF-7, MDA-MB231), Human lung cancer (A-549), human pancreatic cancer (MiaPaca-2), Human prostate cancer (PC-3), Colon cancer cell line (HCT-116, HT 29), wherein, Setomimycin significantly abrogated cancer cell proliferation and inhibited cancer cell migration and invasion in highly metastatic cancer cells (MiaPaca-2, MCF-7, HT-29 and HCT-116) of Pancreatic, Breast and Colorectal origin.

Setomimycin (Compound-3) demonstrates downregulation of ERK and MEK proteins which are the major regulators of cell proliferation, differentiation and apoptosis. Interestingly setomimycin upregulated pro-apoptotic protein Par-4 and down regulated ant-apoptotic protein BCL-2 in Colon as well as breast cancer cells HCT-116 and MCF-7 respectively.

Setomimycin (Compound-3) interacts with MEK1 by forming hydrogen bond with Lys 97, Asp 190 and Ser212 as per molecular docking studies, wherein strong affinity of Setomimycin towards MEK protein was confirmed by Western blot analysis.

EXAMPLES

The following examples are given by way of illustration of the working of the invention in actual practice and should not be construed to limit the scope of the present invention.

Example 1: Isolation and Characterization of *Streptomyces* sp. MTCC-25420 and *Streptomyces* sp. MTCC-25512

The actinobacteria strains *Streptomyces* sp. MTCC-25420 and *Streptomyces* sp. MTCC-25512 were isolated from soil sample collected from Shivalik foothills 32.7266$^0$ N, 74.8570$^0$ E, Jammu, India on Starch-Casein agar (SCA) medium. The pure cultures were maintained and preserved on same medium. The morphological characteristics were investigated on ISP2 and SCA, respectively at 28 °C±2 °C. The mycelial organization and sporulation were observed by light microscopy and scanning electron microscopy (SEM). The cultural characteristics of isolate grown on SCA were observed as powdery white colony with circular and smooth ends. Aerial colonies appear white during early growth and yellow pigmentation starts appearing with time.

Molecular characterization was performed by 16S rRNA gene sequencing using universal primers 27F (5'AGAGTTTGATCCTGGCTCAG-3') and 1492R (5'GGCTACCTTGTTACGACTT-3') using Emerald Amp GT master mix. The 1500 bp amplicon was purified by Gel elution/SAP. The purified product was sequenced by Sanger sequencing and the partial sequence was assembled and submitted to NCBI with Accession numbers MW199142 and OM540363. The culture has been submitted to Microbial Type Culture Collection, India with Accession no. MTCC-25420 and MTCC-25512.

Example 2: Maintenance of Culture

The cultures *Streptomyces* sp. MTCC-25420 and *Streptomyces* sp. MTCC-25512 were maintained on glass test tubes of 18×150 $mm^2$ size having agar slants (Table 1) by transferring a loopful of culture from matured slant and kept for incubation at 28 °C±2 °C for about one week with subsequent sub-culturing after two weeks. The glycerol stocks and lyophilized cultures were kept for long term storage of the culture for future purpose.

TABLE 1

Components of media for preservation of cultures *Streptomyces* sp. MTCC-25420 and Streptomyces sp. MTCC-25512

| Ingredients | (g/L) |
|---|---|
| Starch | 10.0 |
| $KNO_3$ | 2.0 |
| $K_2HPO_4$ | 2.0 |
| Casein | 0.3 |
| $MgSO_4 \bullet {}_7H_2O$ | 0.05 |
| NaCl | 2.0 |
| $CaCO_3$ | 0.02 |
| $FeSO_{4.7}H_2O$ | 0.01 |
| pH | 7.0 |
| Agar | 20.0 |

Example 3: Preparation of Pre-Inoculum and Inoculum

Pre-inoculum was prepared in a narrow mouth 500 mL Erlenmeyer flask containing 150 ml medium (Table 2) by transferring loopful of culture from freshly grown culture. The inoculated medium was incubated at about 28 °C±2 °C for about 48-72 hours on a rotating shaker at 250 rpm.

TABLE 2

Components of media used for pre-inoculum preparation

| Ingredients | (g/L) |
|---|---|
| Soluble starch | 25.0 |
| Soyabean meal | 15.0 |
| Yeast extract | 2.0 |
| $CaCO_3$ | 4.0 |
| pH | 7.0 |

Preferably, 5-10% of pre-inoculum was transferred to 1000 mL Erlenmeyer flasks containing 300 ml seed medium (Table 3). The inoculum was prepared by incubating the flasks at 28 °C±2 °C for about 48-72 hours on a rotating shaker at 250 rpm.

TABLE 3

Components of media used for Seed Inoculum

| Ingredients | (g/L) |
|---|---|
| Glycerol | 100.0 |
| Soyabean meal | 2.0 |
| $CaCO_3$ | 3.0 |
| $K_2HPO_4$ | 1.0 |
| $MgSO_4$ | 1.0 |
| NaCl | 2.0 |
| pH | 7.0 |

Example 4: Production of Tetrahydroanthracenes

Preferably, 5-10% of two days old seed culture (inoculum) was transferred to 1000 mL Erlenmeyer flasks containing 300 ml production media as shown in (Table 4) and incubated at 28 °C±2 °C for 2-10 days on a rotating shaker at 250 rpm followed by liquid-liquid extraction using methanol-ethyl acetate.

TABLE 4

Composition of different media used for setomimycin production

| S. No. | Medium | Composition in g/L |
|---|---|---|
| 1 | PM-1 | Glycerol-20.0; Soyabean meal-20; Sodium chloride-3.0 |
| 2 | PM-2 | Starch-25.0; Soyabean meal-15.0; Yeast extract-2.0; $CaCO_3$-4.0 |
| 3 | PM-3 | Dextrin-1.0; Glucose-1.0; Soyabean meal-5.0; Yeast extract-2.0; $CaCO_3$-1.50 |
| 4 | PM-4 | Glucose-50.0; Glycerol-5.0; Peptone-10.0; Malt extract-1.50; Soyabean meal-10.0; $MgSO_4 \bullet 7H_2O$-1.0; $CaCO_3$-5.0; Beef extract-5.0 |
| 5 | PM-5 | Glucose-2.0; Soyabean meal-10.0; Starch-30.0; Corn Steep liquor-1.0; Peptone-3.0; $CaCO_3$-5.0 |
| 6 | PM-6 | Starch-10.0; $KNO_3$-2.0; Casein-0.30; $K_2HPO_4$ −2.0; $MgSO_4$-0.05, NaCl-2.0 |
| 7 | PM-7 | Starch-10.0; $CaCO_3$-3.0; $K_2HPO_4$-1.0; $(NH_4)_2$ $SO_4$; −2.0 $MgSO_4$-1.0; NaCl-1.0 |
| 8 | PM-8 | Starch-10.0; Casein-10.0; Peptone-1.0; Yeast extract-1.0 |
| 9 | PM-9 | $KNO_3$-1.0; $K_2HPO_4$ −0.5; $MgSO_4$-0.5; NaCl-0.5 g; $FeSO_4$-0.010; Starch-20.0 |
| 10 | PM-10 | Oatmeal-10.0; $MgSO_4$-1.0; KCl-1.0; $KH_2PO_4$-0.5; $K_2HPO_4$-0.5; $CaCl_2$-2.0; Yeast extract-4.0; Malt extract-4.0 |
| 11 | PM-11 | Starch-24.0; Dextrin-46.0; Yeast extract-5.0; Peptone-4.0; Soyabean meal-5.0; $K_2HPO_4$-1.0; $CaCO_3$-1.0; $MgSO_4$-1.0 |
| 12 | PM-12 | yeast extract-1.0; beef extract-1.0; casamino acids-2.0; glucose- 10.0 |
| 13 | PM-13 | Glycerol-10.0; $CaCO_3$ −3.0; $K_2HPo_4$ −1.0; $(NH_4)_2$ $SO_4$; −2 $MgSO_4$-1; NaCl-1.0 |
| 14 | PM-14 | Glycerol-20.0; soluble starch-20.0; peptone-10.0; meat extract-5.0; $CaCO_3$-3.0 |
| 15 | PM-15 | Tryptone-1.0; yeast extract-0.30 |
| 16 | PM-16 | Dextrose-4.0; Yeast extract-4.0; Malt extract-10.0 |
| 17 | PM-17 | Oat meal-2.0; trace salt solution ($FeSO_4 \bullet 7H_2O$-0.01, $MnCl_2 \bullet 4H_2O$-0.01, $ZnSO_4 \bullet 7H_2O$-0.01) |
| 18 | PM-18 | Soluble starch-1.0; $K_2HPO_4$-0.1; $MgSO_4 \bullet 7H_2O$-0.1; NaCl-0.1; $(NH_4)2SO_4$-0.2; $CaCO_3$-0.2; trace salt solution ($FeSO_4 \bullet 7H_2O$-0.01, $MnCl_2 \bullet 4H_2O$-0.01, $ZnSO_4 \bullet 7H_2O$-0.01) |
| 19 | PM-19 | L-Asparagine-0.1; glycerol-1; $K_2HPO_4$-0.1; trace salt solution($FeSO_4 \bullet H_2O$-0.01, $MnCl_2 \bullet 4H_2O$-0.01, $ZnSO_4 \bullet 7H_2O$-0.01) |
| 20 | PM-20 | Peptone-1.0; yeast extract-0.4; $FeSO_4 \bullet 7H_2O$-1.0 |
| 21 | PM-21 | L-Tyrosine-0.10; glycerol-1; $K_2HPO_4$-0.1; trace salt solution ($FeSO_4 \bullet 7H_2O$-0.01, $MnCl_2 \bullet 4H_2O$-0.01, $ZnSO_4 \bullet 7H_2O$-0.01) |
| 22 | PM-22 | Sucrose-3.0; sodium nitrate-0.20; $K_2HPO_4$-0.10; $MgSO_4 \bullet 7H_2O$-0.05; KCl-0.05; $FeSO_4 \bullet 7H_2O$-0.01 |

The solvent extracts were evaluated by weight as well as their HPLC/LCMS profiling for tetrahydroanthracenes production.

Example 5: Effect of pH on Tetrahydranthracenes Production

The culture was grown over a broad pH range from pH 5.0 to 9.0. Inoculum was added in 500 ml Erlenmeyer flask containing 100 mL of production medium with varied pH.

Setomimycin production was highest at pH 6.5-7.5, although production was observed at wide pH range (pH 5.0 to 9.0).

Example 6: Effect of Temperature on Tetrahydranthracenes Production

*Streptomyces* sp. MTCC-25420 and *Streptomyces* sp. MTCC-25512 can be grown over a broad temperature range from 10 °C to about 45 °C. The inoculum was added in 500 mL Erlenmeyer flask containing 100 ml of production medium and flasks were incubated at varied temperatures i.e. 10 °C, 20 °C, 30 °C, 40 °C and 50 °C. Optimum production of tetrahydroanthracenes appears to occur at a temperature of about 20° to 40 °C.

Example 7: Effect of Carbon Sources on Production of Tetrahydroanthracenes

Carbon sources that are essential component for the growth and production of tetrahydroanthracenes and Setomimycin were evaluated. All types of carbon sources i.e. Monosaccharides, Disaccharides and Polysaccharides such as Glucose, Fructose, Sucrose, Mannitol, Glycerol, Pectin, Lactose, Maltose, Mannose, Chitosan, Dextrin, Starch, Xylose, Mollases, Corn steep liquor, Inositol, Chitin, Sorbitol.

Example 8: Effect of Nitrogen Sources on Production of Tetrahydroanthracenes

Various nitrogen sources such as Beef extract, Casein, Soya Meal, Yeast extract, Oatmeal, N/Z amine A, N/Z amine B, Casein hydrolysate, Peptone, Sodium nitrate, Valine, Ammonium nitrate, Urea, Arginine, Asparagine, Ammonium phosphate, Potassium nitrate, Ammonium sulphate support the production of tetrahydroanthracenes.

Example 9: Effect of Agitation and Inoculum Percent on Production of Tetrahydroanthracenes To study the effect of agitation the *Streptomyces* sp. MTCC-25420 and *Streptomyces* sp. MTCC-25512 was grown on selected production medium with agitation range from 50 to 400 rpm and it has been observed that agitation from 100 rpm to 300 rpm supports maximum production of tetrahydroanthracenes with 10% seed inoculum.

Example 10: Production of Tetrahydroanthracene in Fermenter

The time course of tetrahydranthracenes production was evaluated by transferring the freshly grown cultures in Seed inoculum and further to the production medium. The growth and production were evaluated by sampling the fermentation broth after regular intervals. Antibiotic complex formation starts after 24 hours and optimum production was found after 4-8 days of incubation. Tetrahydroanthracene antibiotics were produced in 5 L to 500 L stirred tank bioreactor using modified production medium PM-7 (Table 4) with combination of other ingredients providing additional carbon/nitrogen/minerals and elicitations. The inoculum was prepared using freshly grown culture of vegetative stage in conical flask using PM-2 medium (Table 4). The 5-10% of 2-4 days old inoculum was transferred to the fermenter. For the efficient growth the volume of air used was 0.05 to 1.5 (vvm) with agitation speed of 50 to 400 rpm at 28 °C±2 °C for 2-10 days. Further, the fermented broth obtained after 6 days of incubation was homogenised with 10% methanol for about 2 hours. The homogenised broth was then extracted at least thrice with ethyl acetate in the ratio of (1:1 v/v). The organic phase, thus obtained was concentrated on a rotary evaporator at 50 °C and pure setomimycin was quantified by HPLC. Tetrahydroanthracene formation starts within the 24 hours of incubation and highest production occurs between 4 to 8 days fermentation, wherein Setomimycin yields range from 30 mg/L to 800 mg/L in combination with various carbon and nitrogen sources along with trace elements, elicitors and precursors (Table 5).

TABLE 5

Composition of modified production media used for tetrahydroanthracenes production

| S. No. | Medium | Composition g/L |
|---|---|---|
| 1 | MP-1 | Glycerol-50.0; $CaCO_3$-3.0; $K_2HPO_4$-1.0; Gluconic acid-2.0; $(NH_4)_2$ $SO_4$; −2.0 $MgSO_4$-1; NaCl-2.0 |
| 2 | MP-2 | Glycerol-50.0; $CaCO_3$-3.0; $K_2HPO_4$-1.0; Gluconic acid-2.0; $(NH_4)_2$ $SO_4$; −2.0 $MgSO_4$-1; NaCl-2.0; Valine-1.0 |
| 3 | MP-3 | Glycerol-100.0; $CaCO_3$-3.0; $K_2HPO_4$-1.0; Gluconic acid-2.0; $(NH_4)_2$ $SO_4$; −2.0 $MgSO_4$-1.0; NaCl-2.0 |
| 4 | MP-4 | Glycerol-50.0; $CaCO_3$-3.0; $K_2HPO_4$-1.0; Soyabean meal-2.0; $MgSO_4$-1.0; NaCl-2.0 |
| 5 | MP-5 | Glycerol-50.0; $CaCO_3$-3.0; $K_2HPO_4$-1.0; Soyabean meal-2.0; $MgSO_4$-1.0; NaCl-2.0 valine-1.0 |
| 6 | MP-6 | Glycerol-100; Soyabean meal-2.0; $CaCO_3$-3.0; $K_2HPO_4$-1.0; $MgSO_4$-1.0; NaCl-2.0 |

Further, various carbon & nitrogen sources were used in combination with different trace elements (Table 6) to produce tetrahydroanthracenes from pH 4.0 to 10.0

TABLE 6

Various carbon, nitrogen sources and trace elements used in combination for tetrahydroanthracenes production

| S. No. | Carbon sources | Nitrogen sources | Trace elements |
|---|---|---|---|
| 1 | Glucose | Beef extract | Calcium carbonate |
| 2 | Fructose | Casein | Magnesium sulphate |
| 3 | Sucrose | Soyabean Meal | Di-potassium hydrogen phosphate |
| 4 | Mannitol | Yeast extract | Ferrous sulphate |
| 5 | Glycerol | Oat meal | Potassium chloride |
| 6 | Pectin | N/Z amine A | Sodium chloride |
| 7 | Lactose | N/Z amine B | Ammonium sulphate |
| 8 | Maltose | Casein hydrolysate | Ammonium nitrate |
| 9 | Mannose | Peptone | |
| 10 | Chitosan | Sodium nitrate | |
| 11 | Dextrin | Ammonium nitrate | |
| 12 | Starch | Urea | |
| 13 | Xylose | Ammonium phosphate | |
| 14 | Mollases | Potassium nitrate | |
| 15 | Cornsteep liquor | Ammonium sulphate | |
| 16 | Inositol | Arginine | |
| 17 | Chitin | Asparagine | |
| 18 | Sorbitol | Valine | |

All the biological materials used in the invention were procured from HIMEDIA, Laboratories Pvt. Ltd 23, Vadhani Ind. Est., LBS marg, Mumbai-400086, India.

Example 11: Extraction of Tetrahydroanthracenes from Fermentation Broth

For the extraction of bioactives, the fermented broth obtained after 6 days of incubation was homogenised with 10% methanol for about 2 hours. The homogenised broth was then extracted thrice with ethyl acetate in ratio of 1:1 (v/v). The organic phase thus obtained was concentrated on a rotary evaporator at 50 °C. LC-MS profile of the crude extract indicated the presence of tetrahydroanthracenes compounds in the extract, which were purified by column chromatography/preparatory TLC/preparatory HPLC.

Example 12: Isolation and Characterization of Tetrahydroanthracene Compounds

The isolation of compounds was carried out through open glass gravity column chromatography. Slurry of the crude extract was made using silica 60-120 (5.0 g) which was loaded on a glass column packed with silica 60-120. For purification, elution was carried out by ethyl acetate and thereafter, polarity was increased step by step by adding ethyl acetate to toluene in the order of 5%, 10%, 15% and 20%. A small fraction of 25 mL each was collected and monitored through TLC after charring with anisaldehyde. Fractions were pooled together based on similarity of $R_f$ values of the spots as well as the purity of the isolated fractions. Total seven sub-fractions were collected, wherein fractions 1-3 were further mixed and subjected to silica open glass gravity column and Compounds 1 and 3 was purified, while, Compound 2 was purified from fraction 3-7. The pure sub fractions thus obtained were pooled together and concentrated on rotary evaporator at 30-35 °C under reduced pressure which were further confirmed by $^{1}H$ NMR and $^{13}C$ NMR. The purity of compounds was checked by HPLC chromatography.

Compound 1 was obtained as brown solid having molecular mass of 300.0 as obtained by LCMS fragmentation.

1

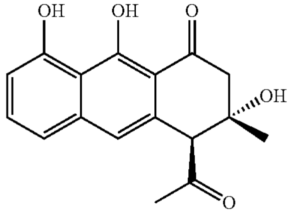

$^{1}H$ NMR (400 MHz, $CDCl_3$) δ 16.28 (s, 1H), 9.76 (s, 1H), 7.51 (t, J=8.0 Hz, 1H), 7.17 (d, J=7.6 Hz, 1H), 7.08 (s, 1H), 6.89 (dd, J=7.9, 0.8 Hz, 1H), 4.18 (s, 1H), 3.50 (d, J=18.3 Hz, 1H), 2.73 (dd, J=18.3, 1.7 Hz, 1H), 2.41 (s, 3H), 1.48 (s, 3H). $^{13}C$ NMR (101 MHz, $CDCl_3$) δ 205.6, 202.5, 166.6, 158.3, 139.0, 133.1, 132.0, 119.3, 118.4, 113.3, 112.0, 108.2, 71.8, 63.0, 47.5, 32.1, 27.5.

The PMR spectra suggest that the compound contains 16 protons: 6 protons from 2 methyl groups, 2 protons from one methylene group, 4 protons from olefinic and/or aromatic moieties, 1 protons a C—H, and 3 protons from 3 hydroxyl groups, and in CMR 17 peaks of carbons were found, 2 in carbonyl region, 2 in aromatic with substitution, 1 in hydroxylated region, 8 in aromatic, 1 in methylene and 2 in methyl region, further, molecular mass of 300.0 as obtained by LCMS fragmentation confirmed the structure of compound 1 as a monomer which is in accordance with literature reports. Two IR spectra revealed that the compound contains C═C and hydroxyl groups. By calculating the 21 degrees of unsaturation and UV absorptions of the compound indicates that it contains naphthocyclinone or anthracyclinone skeleton as a chromophore and it contains no sugar moiety.

Compound 2 was obtained as brown powder with the molecular mass 598.0 as obtained by LCMS fragmentation.

2

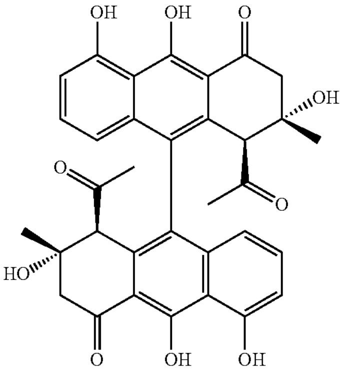

$^{1}H$ NMR (400 MHz, $CDCl_3$) δ 9.98 (s, 2H), 7.20 (dd, J=9.3, 6.8 Hz, 2H), 6.82 (d, J=7.8 Hz, 2H), 6.34 (d, J=8.2 Hz, 2H), 4.16 (s, 2H), 2.93 (d, J=18.5 Hz, 2H), 2.59 (d, J=18.5 Hz, 2H), 1.21 (s, 6H), 1.17 (s, 6H).

$^{13}C$ NMR (101 MHz, $CDCl_3$) δ 205.2, 202.1, 164.7, 157.6, 137.8, 132.5, 132.4, 124.0, 116.6, 111.9, 111.3, 108.6, 70.9, 58.7, 44.7, 32.0, 27.8.

The PMR spectra suggest that the compound contains 30 protons: 12 protons from 4 methyl groups, 4 protons from two methylene group, 6 protons from olefinic and/or aromatic moieties, 2 protons from two C—H, and 6 protons from 6 hydroxyl groups, and in CMR 17 peaks of carbons were found, 2 in carbonyl region, 2 in aromatic with substitution, 1 in hydroxylated region, 8 in aromatic, 1 in methylene and 2 in methyl region, further, molecular mass 580.0 as obtained by LCMS fragmentation confirmed the structure of compound 2 which is in accordance with literature reports. Two IR spectra revealed that the compound contains C═C and hydroxyl groups. By calculating the 21 degrees of unsaturation and UV absorptions of the compound indicates that it contains naphthocyclinone or anthracyclinone skeleton as a chromophore and it contains no sugar moiety.

Compound 3 (Setomimycin) was obtained as red crystalline solid with the molecular mass 580.0 as obtained by LCMS fragmentation.

3

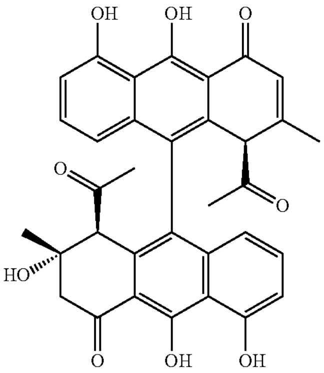

$^{1}H$ NMR (400 MHz, $CDCl_3$) δ 10.04 (s, 1H), 9.93 (s, 1H), 7.33 (t, J=8.0 Hz, 1H), 7.22-7.15 (m, 2H), 6.93 (d, J=7.8 Hz, 1H), 6.83 (d, J=7.9 Hz, 1H), 6.59 (d, J=8.3 Hz, 1H), 6.21 (d, J=7.5 Hz, 2H), 3.94 (s, 1H), 3.63 (s, 1H), 3.12 (d, J=17.6 Hz, 1H), 2.58 (d, J=17.8 Hz, 1H), 1.95 (s, 3H), 1.63 (s, 3H), 1.34 (s, 3H), 1.22 (s, 3H). $^{13}C$ NMR (101 MHz, $CDCl_3$) δ 208.5, 203.3, 199.6, 191.1, 166.5, 164.8, 158.8, 158.5, 158.1, 138.7, 137.0, 134.3, 133.9, 133.5, 133.2, 125.8, 125.1, 124.3, 117.5, 116.5, 114.1, 113.4, 113.0, 112.6, 112.5, 109.3, 108.6, 72.1, 60.9, 60.6, 47.2, 33.9, 29.4, 28.2, 23.0.

The PMR spectra suggest that the compound contains 28 protons: 12 protons from 4 methyl groups, 2 protons from a methylene group, 2 proton from two C—H, 7 protons from olefinic and/or aromatic moieties, and 5 protons from 5 hydroxyl groups, and in CMR, 34 carbons were found, 4 in carbonyl region, 5 in aromatic with substitution, 17 in aromatic, 3 in oxygenated region, 1 in methylene and 4 in methyl region. IR spectra revealed that the compound contains C═C and hydroxyl groups. By calculating the 21 degrees of unsaturation and UV absorptions of the compound indicates that it contains naphthocyclinone or anthracyclinone skeleton as a chromophore and it contains no sugar moiety.

TABLE 7

Minimum Inhibitory Concentrations of Compounds 1-3 against Gram positive bacteria

| Test organism | Compound-1 | Compound-2 | Compound-3 |
|---|---|---|---|
| *Staphylococcus aureus* | 25 | 12 | 8 |
| *Bacillus cereus* | 12 | 6 | 4 |
| *Bacillus subtilis* | 12 | 6 | 16 |
| *Micrococcus luteus* | 6 | 4 | 8 |

Example: 14 Anticancer Activity of Compounds (1-3) Against Panel of Cancer Cell Lines Compound Setomimycin showed potent anticancer properties against diverse range of cancer cells of different origin as shown in Table 8. $5\times10^3$ cells were seeded/well in a 96 well plate and treated with Compounds (1-3) for 48 hours with 100 μM concentration range to a panel of cancer cell lines. After 44 hour MTT with final concentration of 0.5 mg/ml were added to cells and incubated for 4 hour at 37 °C until formazon crystals are formed. MTT was removed and formazon crystals were lysed by DMSO for 30 minutes at 37 °C, the absorbance was measured at 570 nM and the $IC_{50}$ values were calculated using graph pad prism.

TABLE 8

Cytotoxicity ($IC_{50}$) of Compounds (1-3) against different cancer cells of Colon, Breast, Lung, Pancreatic and Prostrate origin

| | Cell lines | | | | | | | | |
|---|---|---|---|---|---|---|---|---|---|
| Compounds | MCF-7 | HT-29 | MDA-MB-231 | A549 | MiaPaca-2 | PC3 | HCT-116 | Panc-1 | FR2 |
| Compound-1 | 9.56 | 8.64 | 13.6 | 38.91 | 12.72 | 14.72 | 10.36 | 15.62 | 48.7 |
| Compound-2 | 11.22 | 15.45 | 12.52 | 38.73 | 8.31 | 17.47 | 18.91 | 21.31 | 62.31 |
| Compound-3 | 6.9 | 4.2 | 7.5 | 11.45 | 4.57 | 7.02 | 5.3 | 48 | 53.29 |

Example: 13 Minimum Inhibitory Concentration of Setomimycin

The minimum inhibitory concentrations (MIC) of purified compound showing significant zones of inhibition in the preliminary antimicrobial assay using agar well diffusion method were evaluated. MIC assay was carried out by a microtiter broth dilution method with some modifications. Stock solution of each pathogen was prepared in normal saline solution i.e. 0.85% NaCl (w/v) at a concentration of $10^8$ cells/ml and finally diluted with respective growth media to give approximately $10^5$ CFU/ml for all organisms. Different dilutions of compound was prepared (2-500 μg/ml) by serial dilutions. 100 μl of each concentration (2-500 μg/ml) of the compound was loaded onto each well and was mixed with 100 μl of diluted pathogens containing $10^5$ CFU/ml. Each plate had a set of controls: a column with broad-spectrum antibiotics (ciprofloxacin) as positive controls, a column without compound, and one without the relevant test organism. The microtitre plates were then incubated overnight at 37 °C for bacterial pathogens and 28 °C for fungal pathogens and were analysed after incubation. The lowest inhibitory dilution, at which there was no visible growth, was considered as MIC as shown in Table 7.

Example 15: Antiproliferative Properties of Setomimycin

Figure 2:
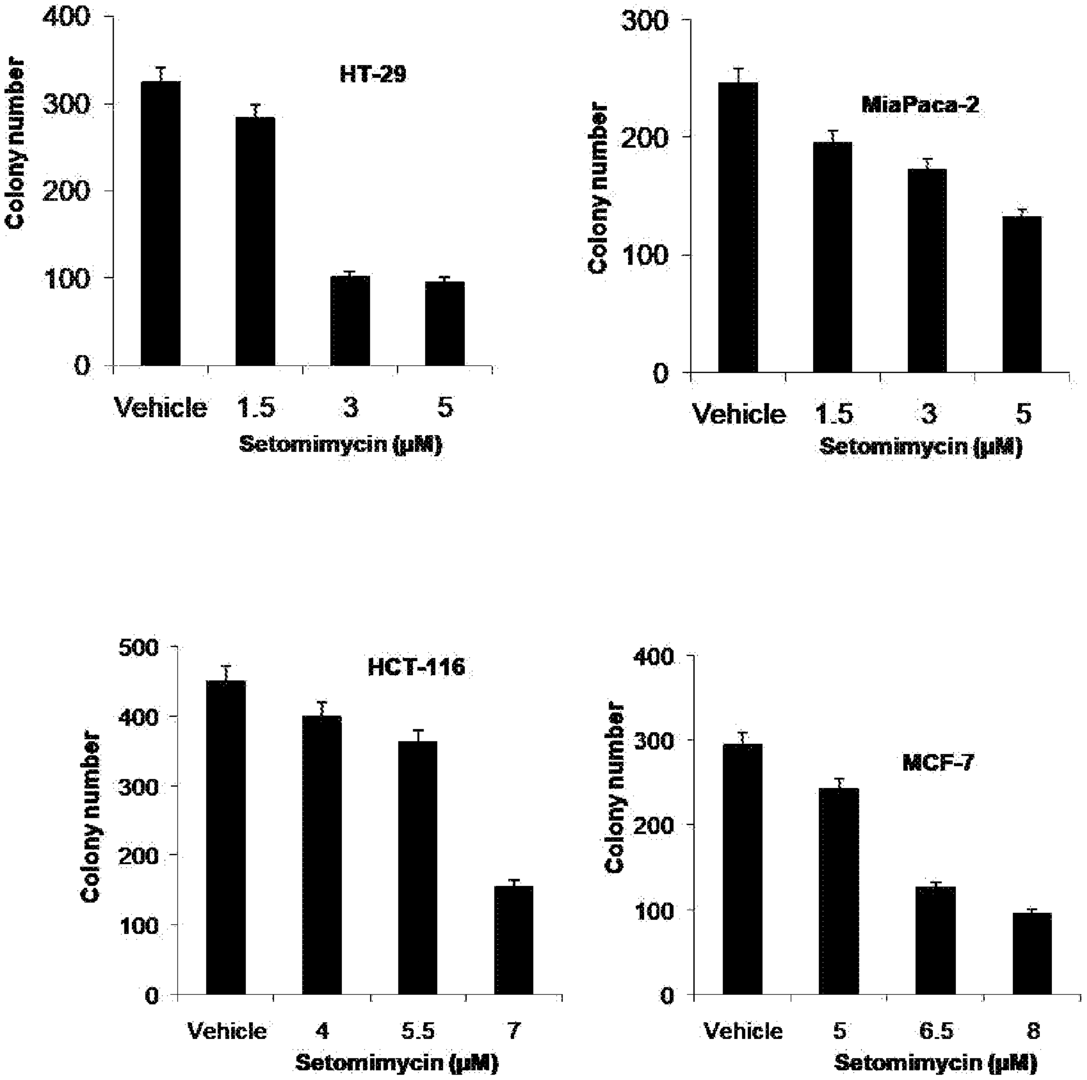
FIG. 2 represents anti-proliferative property of Setomimycin in HT-29, MiaPaca-2, HCT-116 and MCF-7 cell lines

Colony formation assay was performed to further certify the antiproliferative properties of setomimycin in four different cancer cell lines viz. HT-29, MiaPaca-2, HCT-116 and MCF-7. Interestingly, setomimycin showed promising results near the $IC_{50}$ values across all four cell lines as shown in FIG. 2. Cells were seeded onto 6 well plates at seeding density $1\times10^3$ cells/well and treated with increasing concentration of setomimycin nearby the $IC_{50}$ values for 5 days. Upon termination the cells were stained with 0.1% crystal violet for 20-30 minutes and washed with $dH_2O$ thoroughly. The images were taken from plates with NIKON camera (D3100). Average colonies (n=3) were quantified from different fields. Bar graphs represent the number of colonies (n=3, error bars indicate ±SD).

Example 16: Anti-Invasive Properties of Setomimycin

Figure 3:
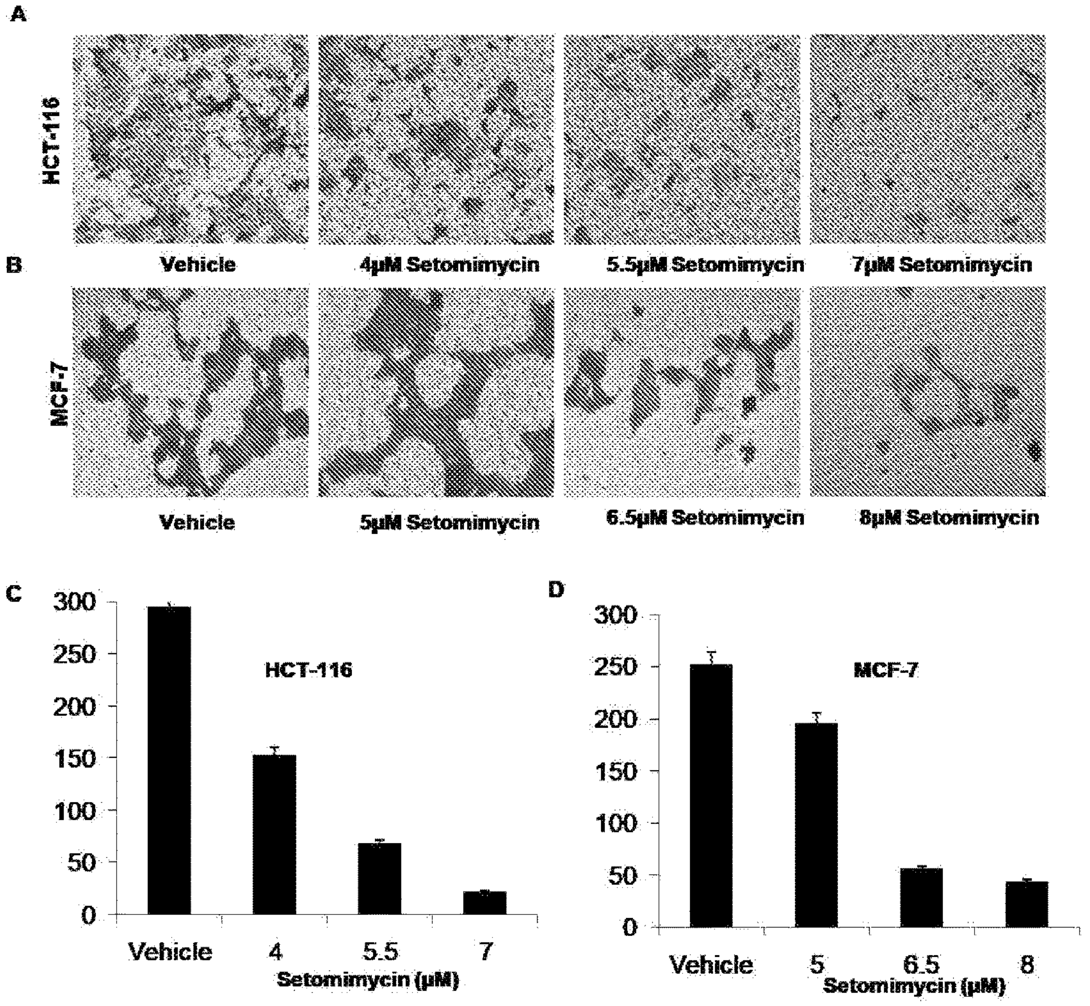
FIG. 3 represents inhibition of cancer cell invasion by Setomimycin (Compound-3).

The above results depict significant antiproliferative effects of setomimycin in different cell lines near $IC_{50}$ values. Transwell invasion assay was performed to check the anti-invasive properties of setomimycin. Interestingly the invasion of the cells from the upper chamber of insert were significantly inhibited to the lower chamber where growth medium with fetal bovine serum was present acting as the chemoattractant with increasing concentration of setomimycin in HCT-116 as well as MCF-7 as shown in FIG. 3.

(A-B) $1.2\times10^6$ HCT-116 and MCF-7 cells were seeded in the upper chamber of inserts in serum free medium and treated with indicated concentration of setomimycin for 48 hours. After 48 hours the invaded cells from lower insert were fixed with ice cold methanol and stained with 0.1% crystal violet for 20-30 minutes. After staining the inserts were washed with $dH_2O$ thoroughly and cells from three different fields in each treated condition were counted and photographed under an inverted microscope (20× magnifications). (C-D) Bar graph representing the number of invaded cells (n=3, error bars indicate ±SD).

Example 17: Anti-Migratory Property of Setomimycin

Figure 4:
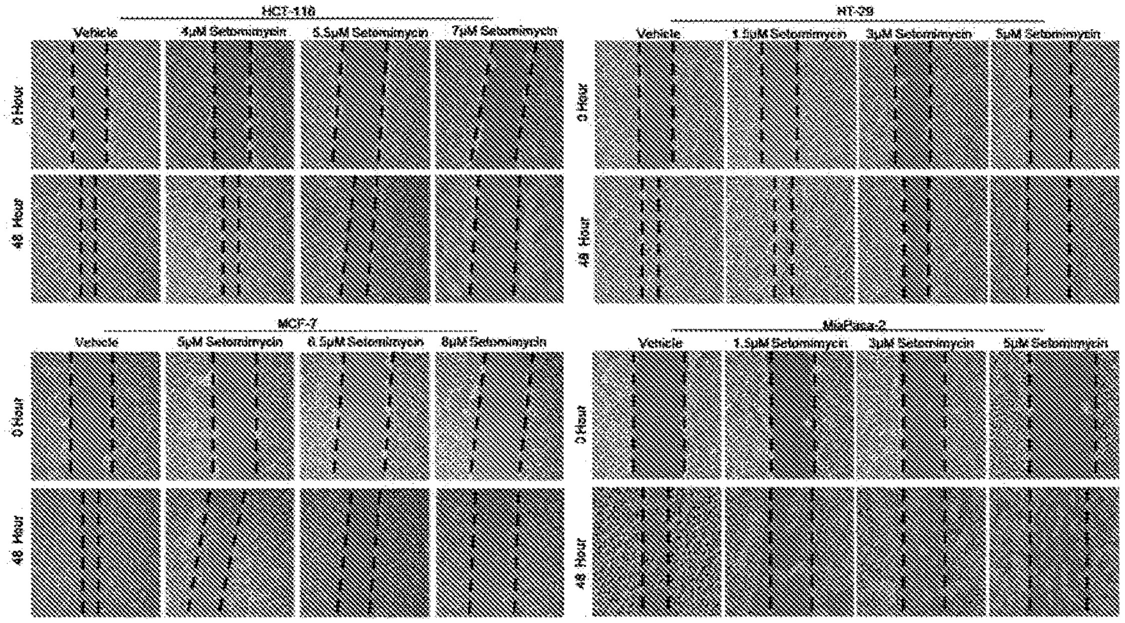
FIG. 4 represents Setomimycin (Compound-3) showing anti migratory properties.

Scratch assay was performed in the panel of cancer cell lines with varying degree of invasive and migratory capabilities as shown in FIG. 4. Our results unveiled that setomimycin inhibited the migratory potential of all the cell lines treated with different concentration of setomimycin within the range of their $IC_{50}$ values. Interestingly setomimycin inhibited the cell migration in HCT-116 and MCF-7 as well as most aggressive cell lines like HT-29 and MiaPaca-2 as well. These results portray the anti-metastatic properties of setomimycin.

$5\times10^5$ cells were seeded onto 6 well plate and grown upto more than 90% confluency. After the proper attachment of cells wounds were created with the help of a 20-200 μL sterile pipette tip. Subsequently the cells were treated with indicated concentration of setomimycin and vehicle (DMSO). The images were taken under inverted microscope at 20× magnification.

Example 18: Docking Study of Setomimycin on Cancer Targets

The molecular docking studies were performed using GLIDE module of Schrödinger software. For molecular docking crystal structure of V600E oncogenic mutant BRAF (4XV2), ERK1 (4QTB), ERK2 (6GDQ), MEK1 (3SLS), Src (4MXO) and STAT3 (6NUQ) was downloaded from RCSB protein data bank. Docking of co-crystalised ligands to its respective target using XP precision generated poses with similar orientation and less RMSD with respect to co-crystalised ligand. Thus, further studies were carried out using Glide XP mode. Among all the targets, the antibiotic setomimycin showed the highest docking score (−6.808 kcal/mol) with the target MEK1 (Table 9). Moreover, the dock score of setomimycin, in comparison to the known inhibitors of the selected targets, was the highest in case of MEK1. The rescoring of the top docking pose of setomimycin was done by calculating DG-binding with MMGBSA and it showed the highest binding affinity (−43.77 kcal/mol) with MEK1. It was further observed that setomimycin interacts with MEK1 by forming hydrogen bond with Lys 97, Asp 190 and Ser212. Lys 97 helps in the binding of ATP to MEK1. Asp 190 is an important catalytic residue involves in the abstraction of a proton of a threonine or tyrosine on ERK1/2. Most of the reported inhibitors act by binding with these residues. Therefore, setomimycin may exhibit anti-proliferative properties by inhibiting MEK1.

TABLE 9

Docking score of Setomimycin with various cancer targets

| Target Protein | Docking score (kcal/mol) |
|---|---|
| BRAF | −6.148 |
| ERK1 | −4.830 |
| ERK2 | −4.721 |
| MEK1 | −6.808 |
| Src | −5.106 |
| STAT3 | −2.122 |

Figure 5:
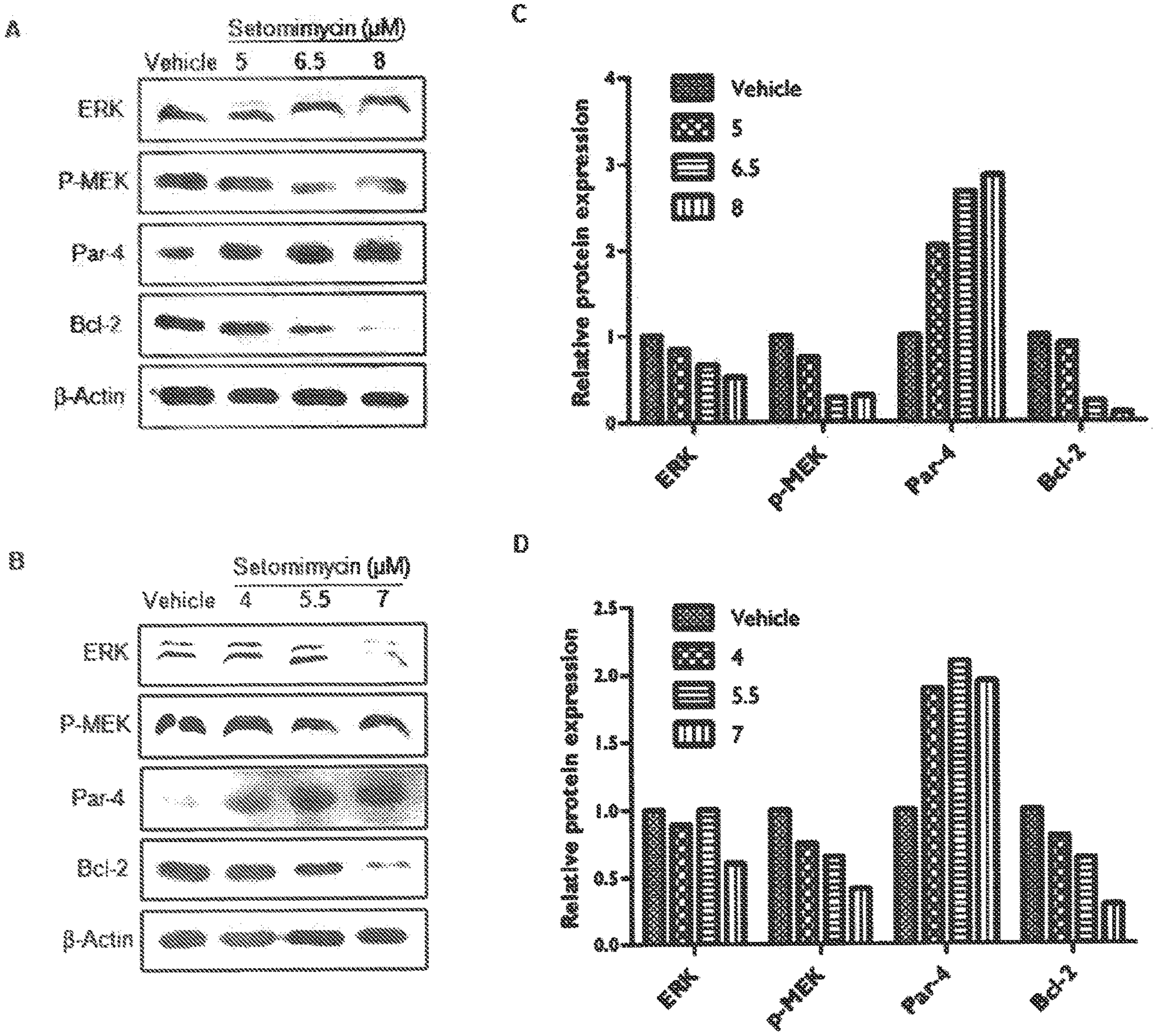
FIG. 5 Illustrates effect of setomimycin (Compound-3) pro-proliferative and anti-apoptotic protein targets in cancer cells: (A-B) Immunoblot analysis of ERK, p-MEK, Par-4, BCL-2 and β-actin in HCT-116 and MCF-7 cells treated with setomimycin for 48 h. (C-D) Densitometry analysis showing relative protein expression for the western blots presented

Example 19: Effect of Setomimycin on Anticancer Target Pathways and Apoptosis Strong active potential of setomimycin against tumor cell proliferation and migration at nearby concentration of $IC_{50}$ values was depicted by MTT data. Further, molecular docking studies predicted the strong affinity of setomimycin targeting MEK pathway. ERK and MEK are the major signaling pathways regulating cancer cell proliferation, differentiation and apoptosis. Therefore, Western blotting was carried out to check the effects of Setomimycin on ERK and MEK proteins. Phospho MEK was found to be down regulated with increasing concentration of setomimycin validating it as antitumor candidate. Interestingly, Par-4 which is a pro-apoptotic protein was upregulated and BCL-2 an antiapoptotic protein was downregulated by Setomimycin. These results demonstrate the strong antitumor capability of Setomimycin regulating proliferation and metastasis, which further induces pro-apoptotic marker as well, diminishing the expression of anti-apoptotic proteins as shown in FIG. 5.

Advantages of the Invention

The main advantages of the present invention are:

It provides an improved and efficient process for tetrahydroanthracenes production from *Streptomyces* sp. MTCC-25420 and *Streptomyces* sp. MTCC-25512, wherein much higher yields are obtained in short fermentation cycle as compared to the previous reports.

Production upto 5.0 g/L extract of tetrahydroanthracenes can be achieved under specified fermentation conditions in combination of production media and certain elicitors/precursors Setomimycin yields of 800 mg/L or even higher could be achieved in specified fermentation conditions and in the presence of certain elicitors/precursors, which is much higher than the reported yields Setomimycin has shown activity against different cancer cell lines of Colon, Breast, Lung, Pancreatic and Prostrate origin.

Setomimycin significantly abrogated cancer cell proliferation and inhibited cancer cell migration and invasion in highly metastatic cancer cells (MiaPaca-2, MCF-7, HT-29 and HCT-116) of Pancreatic, Breast and Colorectal origin.

Strong antitumor capability of Setomimycin has been demonstrated by regulating proliferation and metastasis, which further induces pro-apoptotic marker as well, diminishing the expression of anti-apoptotic proteins.

We claim:

1. A process for the preparation of tetrahydroanthracene compounds of Formula I from *Streptomyces* sp. MTCC-25420 and *Streptomyces* sp. MTCC-25512

Formula I

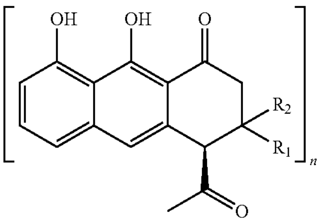

wherein n=1 or 2 and $R_1$=$CH_3$; $R_2$=OH, the process comprising:

i. isolating the *Streptomyces* sp. MTCC-25420 and the *Streptomyces* sp. MTCC-25512 strains from soil samples;

ii. preparing a seed inoculum from the isolated strains the *Streptomyces* sp. MTCC-25420 and *Streptomyces* sp. MTCC-25512 as obtained in step (i) and transferring 5-10% of two days old seed culture to a production medium containing 1 to 15 w/v % of a carbon source, 2 to 10% of a nitrogen source, and trace salts at pH in the range of 4.0 to 10.0, followed by incubating at a temperature in a range of 15 °C-45 °C for a period in range of 2-10 days on a rotating shaker at a speed in a range of 50-400 rpm to obtain fermented broth;

iii. initiating fermentation, in a 5-500 L bioreactor, by inoculation of 10% inoculum as obtained in step (ii) in production medium having 50.0 g/L of glycerol, followed by glycerol feeding at a rate of 2 g/L/hr after 24 hours of incubation until a final glycerol concentration of 150 g/L is achieved in a modified production medium with 10 LPM air at 100 rpm agitation;

iv. conducting liquid-liquid extraction of fermented broth of 4 to 5 days as obtained in step (ii) and (iii) using solvents from the group methanol, ethyl acetate, toluene, and any combination thereof to obtain 200 mg/L to 5 g/L tetrahydroanthracenes of Formula I;

v. purifying the extract obtained from step (iv) by single step gravity column chromatography by elution, followed by step-by-step elutions with 5%, 10%, 15% and 20% of Toluene in ethyl acetate to obtain the tetrahydroanthracene compounds of Formula I.

2. The process as claimed in claim 1, wherein the tetrahydroanthracenes comprising a structure of Formula I are selected from the group consisting of Compound 1, Compound 2 and Compound 3:

Compound 1

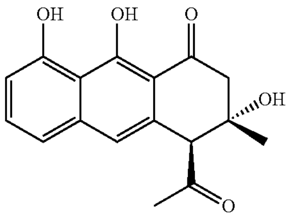

4-acetyl-3,8,9-trihydroxy-3-methyl-3,4-dihydroanthracen-1(2H)-one

Compound 2

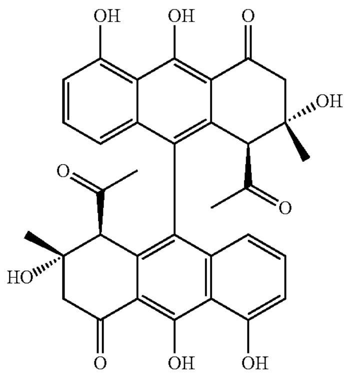

1,1′-diacetyl-2,2′,5,5′,10,10′-hexahydroxy-2,2′-dimethyl-2,2′,3,3′-tetrahydro-[9,9′-bianthracene]-4,4′(1H,1′H)-dione -continued Compound 3

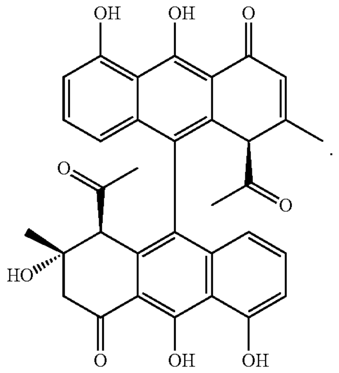

1,1′-diacetyl-2,5,5′,10,10′-pentahydroxy-2,2′-dimethyl-2,3-dihydro-[9,9′-bianthracene]-4,4′(1H,1′H)-dione

3. The process as claimed in claim 1, wherein carbon source is selected from the group consisting of monosaccharides, disaccharides, polysaccharides and any combination thereof.

4. The process as claimed in claim 1, wherein the nitrogen source is beef extract, meat solubles, corn meal, casein, soyabean meal, yeast extract, N/Z amine A, N/Z amine B, casein hydrolysate, enzyme-hydrolyzed casein, valine, nitrate salts or any combination thereof.

5. The process as claimed in claim 1, wherein the trace salts are selected from the group consisting of calcium carbonate, magnesium sulphate, di-potassium hydrogen phosphate, ferrous sulphate, potassium chloride, sodium chloride, ammonium sulphate, and ammonium nitrate.

6. The process as claimed in claim 2, wherein Compounds 1-3 exhibit anticancer activity in breast cancer cell lines, human lung cancer cell lines, human pancreatic cancer cell lines, human prostate cancer cell lines, and colon cancer cell lines.

7. The process as claimed in claim 2, wherein Compound 3 inhibits cancer cell proliferation and migration of metastatic cancer cell lines of pancreatic, breast and colorectal origin.

8. The process as claimed in claim 2, wherein Compound 3 down-regulates ERK and MEK proteins.

9. The process as claimed in claim 1, wherein carbon source is glucose, fructose, sucrose, mannitol, glycerol, gluconic acid, pectin, lactose, maltose, mannose, chitosan, dextrin, molasses, starch, xylose, corn steep liquor, inositol, chitin, sorbitol, or any combination thereof.

10. The process as claimed in claim 2, wherein Compound 3 up-regulates pro-apoptotic protein Par-4.

11. The process as claimed in claim 2, wherein Compound 3 down-regulates anti-apoptotic protein BCL-2.

12. The process as claimed in claim 2, further comprising isolating Compounds 1-3 from each other via chromatography.

13. The process as claimed in claim 12, wherein the chromatography comprises High-Performance Liquid Chromatography (HPLC).

14. The process as claimed in claim 4, wherein the nitrate salts are sodium nitrate, ammonium nitrate, potassium nitrate and any combination thereof.

* * * * *